United States Patent [19]

Otagiri et al.

[11] Patent Number: 5,424,194
[45] Date of Patent: Jun. 13, 1995

[54] 4-(CYANOMETHYLTHIO)PHENOL ENHANCED PEROXIDASE ASSAYS

[75] Inventors: Ken Otagiri; Masakazu Sugiura, both of Kyoto; Katsushige Kouge; Tatsuya Koizumi, both of Yamaguchi, all of Japan

[73] Assignee: Sanyo Chemical Industries, Ltd., Kyoto, Japan

[21] Appl. No.: 102,542

[22] Filed: Aug. 5, 1993

Related U.S. Application Data

[63] Continuation of Ser. No. 853,835, Mar. 19, 1992, abandoned.

[30] Foreign Application Priority Data

Mar. 20, 1991 [JP] Japan .................................. 3-81922

[51] Int. Cl.$^6$ .................. G01N 33/543; G01N 33/535
[52] U.S. Cl. ...................................... 435/7.9; 435/7.5; 435/7.92; 435/7.93; 435/7.94; 435/7.95; 435/28; 435/968; 435/975
[58] Field of Search ................... 435/7.5, 7.9, 28, 968, 435/975; 436/537; 252/700

[56] References Cited

U.S. PATENT DOCUMENTS 4,598,044  7/1986  Kricka et al. .................... 435/28

FOREIGN PATENT DOCUMENTS 0267582  5/1986  European Pat. Off. .

OTHER PUBLICATIONS

Catalogue of Aldrich Chemical Company (1990) p. 890.
Thorpe et al, Methods in Enzymology, vol. 133, pp. 331–353 (1986).
"Clinical Chem." H. G. Thorpe et al; vol. 31, No. 8. p. 1335 (1985).

*Primary Examiner*—Carol A. Spiegel
*Assistant Examiner*—Lora M. Green
*Attorney, Agent, or Firm*—Birch, Stewart, Kolasch & Birch

[57] ABSTRACT

A chemiluminescent reaction, which may be utilized as an immunoassay, carried out by 2,3-dihydro-1,4-phthalazinedione or its derivative, a peroxidase, and an oxidant, is enhanced by adding a phenolic compound such as (4-cyanomethylthio)phenol thereto. Especially, it is preferred that (4-cyanomethylthio)phenol is added to a mixture of luminol, horseradish peroxidase, and hydrogen peroxide to provide a significantly enhanced and stabilized luminescent reaction. Involving this enhanced luminescent reaction to an immunoassay, the sensitivity of the assay may be increased.

14 Claims, 3 Drawing Sheets

Fig. 1 Luminescent pattern of luminol added (4-cyanomethylthio)phenol

Fig. 2 Comparison of enhancing effects

Fig. 3 Calibration curve of chemiluminecent immunoassay indicating AFP.

Fig. 4 Correlation of AFP assay by chemiluminescent and chromometric immunoassay Fig. 5 Calibration curve of chemiluminescent immnoassay indicating T4.

Fig. 6 Correlation of EIA assay indicating chemiluminescent and chromometric immunoassay

4-(CYANOMETHYLTHIO)PHENOL ENHANCED PEROXIDASE ASSAYS

This application is a continuation of application Ser. No. 07/853,835 filed on Mar. 19, 1992, now abandoned.

This invention relates to a luminescent and luminometric assay which is carried out by 2,3-dihydro-1,4-phthalazinedione or its derivative, a peroxidase enzyme, and an oxidant, in the presence of an enhancer. Furthermore, this invention relates to a diagnostic kit for use in the luminescent or luminometric assay comprising 2,3-dihydro-1,4-phthalazinedione or its derivative, a peroxidase, an oxidant., and an enhancer. Particularly the kit may utilize an immunoassay.

DESCRIPTION OF THE PRIOR ART

Gary H. G. Thorpe et al. disclose that a chemiluminescent reaction involving 2,3-dihydro-1,4-phthalazinedione or its derivative, a peroxidase enzyme, and an oxidant is carried out in the presence of a halogenated phenol such as paraiodophenol, and thus the chemiluminescent reaction is enhanced (*Clinical Chemistry*, vol.31, No. 8, p.1335)). Kricka et al. disclose methods of carrying out an assay or an immunoassay wherein the above-mentioned luminescent reaction is carried out by using a certain type of phenolic compound as an enhancer (U.S. Pat. No. 4,598,044). Further, in an assay of substances in biological fluids, there is widely known the enzyme immunoassay (EIA), wherein said substances or an antigen of said substances are labelled by a peroxidase, and activity of the peroxidase is assayed by a colorimetric assay involving an oxidant and (o-)phenylenediamine, which is a chromogen.

In the above-mentioned chemiluminescent, if an enhancer which provides more of luminescence with less background and which can be used in smaller amounts is applicable in a luminometric assay, this provides a wider range of application.

SUMMARY OF THE INVENTION

It is an object of this invention to enhance a chemiluminescent of 2,3-phthalazinedione or its derivative, a peroxidase enzyme, and an oxidant.

It is another object of the present invention to provide an assay and immunoassay which are an improved method of detecting and measuring 2,3-dihydro-1,4-phthalazinedione or its derivative, or a peroxidase enzyme by employing the above-mentioned chemiluminescent.

It is a further object of the present invention to provide an assay kit for use in the above-mentioned enhanced chemiluminescent comprising 2,3-dihydro-1,4-phthalazinedione or its derivative, an oxidant, and a peroxidase enzyme. According to the aspects of the present invention therefore, there is provided a chemiluminescent wherein the luminescent reaction is carried out involving a peroxidase enzyme, an oxidant, and a phenolic derivative of general formula(1):

wherein n represents an integer of 1 to 5; R represents phenyl group including phenyl group containing a halogen atom, hydrogen, cyano group, morpholino group, carboxylic acid group, alkoxycarbonyl group of 2 to 7 carbon atoms, metallic carboxylate group, amido group; aldehyde group, and allyl group; A is a hydrogen atom or a halogen atom; X is a hydrogen or alkaline metal. Conditionally, OX and $S(CH_2)_n$—R are in the ortho position or in the para position.

It is a still further object of the present invention to provide an assay of peroxidase enzyme, 2,3-dihydro-1,4-phthalazinedione or its derivative involving the above-mentioned chemiluminescent, and an immunoassay involving this assay.

Yet a further object of the present invention is to provide an assay kit comprising phenolic derivative of general formula (1), 2,3-dihydro-1,4-phthalazinedione or its derivative, an oxidant, and a peroxidase.

In the chemiluminescent reaction of this invention, which is enhanced by using the phenolic derivative of general formula (1), light emission is, comparing with in the case of not using phenolic derivatives, significantly enhanced. In addition, there may be obtained a stabilized luminescent. Also, comparing with a conventional enhanced luminescent reaction, there is provided greater luminescence, and a larger ratio to background. Therefore, utilizing the luminescent reaction, the luminometric assay and the assay kit of the present invention is capable of providing an assay with higher sensitivity. In particular, it is effective for an immunoassay to increase its sensitivity.

It is convenient to use an assay kit of the present invention containing the materials to be used in an assay procedure in order to utilize an excellent luminometric assay with the enhanced chemiluminescent reaction according to this invention.

The major use of chemiluminescent and luminometric assay is in clinical laboratories or doctors' surgeries. The assay kit of this invention may be utilized to assay antigens, for example: tumor marker such as AFP, CEA, ferritin, and the like; hormones such as TSH, LH, FSH, insulin, and the like; hapten hormones such as cortisol, T3, and T4; drugs such as digoxin, and theophylline; infectious substances such as hepatitis antigen; antibodies such as hepatitis antibody, and IgE; and the like.

Other objects and advantages of this invention will be apparent from the following detailed description.

DETAILED DESCRIPTION OF THE INVENTION

Concrete embodiment and examples of this invention will be described hereinafter.

First, substances comprising a phenolic derivative (a), 2,3-dihydro-1,4-phthalazinedione or its derivative (b), a peroxidase enzyme (c) and an oxidant (d) which may be employed in the present invention will be described in detail. The phenolic derivative (a) of a general formula (1) is employed as an enhancer of a luminescent reaction are which exemplified by the followings: (4-benzylthio)phenol, (4-fluorobenzylthio)phenol, (4-bromobenzylthio)phenol, (4-chlorobenzylthio)phenol, (4-iodobenzylthio)phenol, (4-methylthio)-phenol, (4-cyanomethylthio)phenol, (4-cyanoethylthio)phenol, (4-cyanopropylthio)phenol, (4-cyanobutylthio)phenol, (4-cyanobenzylthio)phenol, (4-morpholinomethylthio)phenol, (4-aminomethylthio)phenol, (4-nitromethylthio)phenol, (4-hydroxyphenylthio)acetic acid, (4-hydroxyphenylthio)acetaldehyde, (4-hydroxyphenylthio)acetamide, (4-allylthio)phenol, 4-cyanomethylthio-2-fluorophenol, 4-cyanomethylthio-2-chlorophenol, 4-cyanomethylthio-2-bromophenol, 4-cyanomethylthio-2-iodophenol, and sodium or potassium salts, of these. Among these, preferred are (4-benzylthio)phenol, (4-methylthio)phenol, (4-cyanomethylthio)phenol, (4-morpholinomethylthio)phenol, 4-cyanomethylthio-2-fluorophenol, 4-cyanomethylthio-2-chlorophenol, 4-cyanomethylthio-2-bromophenol, and 4-cyanomethylthio-2-iodophenol, and sodium or potassium salts of these. Most preferred are (4-cyanomethylthio)phenol, 4-cyanomethylthio-2-fluorophenol, 4-cyanomethylthio-2-chlorophenol, 4-cyanomethylthio-2-bromophenol, and sodium or potassium salts of these forementioned.

The 2,3-dihydro-1,4-phthalazinedione or its derivative (b) which is used in this invention is shown in general formula (2):

(2)

wherein $R_1$, $R_2$, $R_3$, and $R_4$ are respectively a hydrogen atom, optionally unsubstituted or substituted $C_1$ to $C_6$ alkyl, optionally unsubstituted or substituted $C_1$ to $C_6$ alkenyl, hydroxyl, $C_1$ to $C_6$ alkoxyl, carboxyl, amino or substituted amino group. Conditionally, at least one of $R_1$ or $R_2$ is an amino or substituted amino group.

Among the above compounds, preferred are luminol, isoluminol, N-aminohexyl-N-ethylisoluminol (abbreviated to AHEI hereinafter), and N-aminobutyl-N-ethylisoluminol (abbreviated to ABEI hereinafter). The most preferred is luminol.

The 2,3-dihydro-1,4-phthalazinedione or its derivative (b) which is used in the assay of this invention may be used in a form, depending on the type of assay, coupled to a ligand such as an antigen, antibody, hapten, protein, avidin, and biotin, or in a free form. In this case, preferred ligands are antigen and antibody. The ligand may be coupled directly to the 2,3-dihydro-1,4-phthalazinedione or its derivative (b) or via a coupling agent. As the coupling agents, for example, conventional N-(m-maleimidobenzoyloxy)succinimide. (MBS) may be employed. (T. Kitagawa et al: *J. Bio. Chem.*, vol.79 p. 233~236 (1976)). As the photon quantum yield of luminol or isoluminol which are coupled to a ligand is reduced, it is preferred to use AHIE or ABEI.

The peroxidase enzyme (c) which is used in this invention include peroxidase extracted from horseradish, for example, milk, leukocyte, and the like. Preferred is peroxidase enzyme extracted from horseradish.

Suitable peroxidase enzyme (c) which is used for luminometric assay of this invention may either be coupled to a ligand such as antigen, antibody, hapten, protein, abizin or biotin, or be free, depending upon the type of the assay. In this case, the preferred ligand is antigen. The ligand may directly coupled to peroxidase enzyme or via a coupling agent. Preferable coupling agent will be well known N-(m-maleimidobenzoyloxy)succinimide (MBS)).

Suitable oxidant (d) which is used in this invention may include hydrogen peroxide, sodium perborate, potassium perborate, and the like. Preferred is a hydrogen peroxide.

To the assay of this invention, surfactant, bovine serum albumin, casein, gelatin, and the like may be added, if necessary.

The conditions for working of this invention will be described in detail.

The luminescent reaction of the present invention is preferably conducted under moderate conditions of temperature, ranging from 5 to 50° C., and pH greater than 6; most preferably, the reaction is to be conducted under conditions of temperature ranging from 10 to 50° C. and pH in the range of 6 to 11 Suitable buffer solution which are used in the method of the present invention may be any type of buffers which are in the above-mentioned range. Among those buffers, preferred are phosphate buffer, glycine/NaOH buffer, Tris/HCL buffer, Tris/acetic acid buffer, carbonate buffer, barbital buffer, and borate buffer. The concentrations of the forementioned buffers are preferred to be from 1 to 1000 mmol/l.

The concentrations of reaction substances which may be used in a luminescent reaction or luminometric assay excluding the substances to be assayed, are generally kept constant. The concentration of a respective reaction substance is determined by depending on luminescent reaction, an object of the assay, method, and conditions. In general, suitable concentrations whereof the luminescent reaction or luminometric assay to be conducted are as following: the phenolic derivative (a) of general formula (1) is preferred to be $10^{-4} \sim 1$ (g/dl).

2,3-dihydro-1,4-phthalazinedione or its derivative (b) is preferred to be 100 nmol $\sim$ 1 mol/liter, the peroxidase (c) is preferred to be 1 ng $\sim$ 5000 mg/liter, and the oxidant (d) is preferred to be 100 nmol $\sim$ 1 mol/liter.

Furthermore, luminometric assay of the present invention is described in detail. The light emitted may be quantified on a conventional luminometer (e.g., Luminesence Reader, made by Alka Co.).

As there are two types of immunoassay, homogeneous and heterogeneous, the luminometric assay of the present invention may be applied to both of these. The homogeneous immunoassay and heterogeneous immunoassay wherein the luminometric assay of the present invention is applied will be described hereinafter.

In a homogeneous immunoassay, for example, either 2,3-dihydro-1,4-phthalazinedione or its derivative (b), or a peroxidase enzyme (c), both of which are contained in the assay kit of the present invention, is sealed into a liposome. A ligand such as antigen, antibody, hapten, protein, avidin, or biotin is immobilized onto the surface of this liposome. Then an antigen-antibody reaction is carried out between the ligand in the sample and the immune-substance which is immobilized onto the surface of the liposome; consequently, the amount of the peroxidase or luminol which are derived from the liposome is quantified by conducting a luminometric assay involving a phenolic derivative (a) of a general formula (1) and an oxidant (d); and thus the ligand in the sample may be assayed.

The other type of immunoassay, heterogeneous immunoassay is a method which is widely used for routine analysis in examination laboratories is divided broadly into two categories comprising: (1) two-site heterogeneous immunoassay; (2) competitive heterogeneous immunoassay. The luminometric assay of the present invention is applicable to either or both heterogeneous immunoassays.

In two-site heterogeneous immunoassay, a ligand such as antigen, antibody, hapten, protein, avidin, or biotin is immobilized on a carrier such as a test tube, glass beads, plastic beads, micro-particles, and the like, the sample is added thereto, then an antigen-antibody reaction is carried out therein. Secondly, unreacted reactants are removed enzyme-labelled ligand is added, and an antigen-antibody reaction is carried out therein with the substances to be assayed in the sample which has been reacted and/or bound to the ligand which has been immobilized in the first step of the reaction.

Heterogeneous immunoassay employing two-site heterogeneous immunoassay may include a conventional enzyme immunoassay, involving a solid phase antibody wherein an antiferritin-antibody is immobilized on a test tube made of polypropylene, and antiferritin-antibody which is labelled by peroxidase. Enzyme activity is assayed by colorimetric assay involving a chromogen, 2,2'-azino-di(3-ethylbenzthiazoline-6-sulfonate) (ABTS), and the concentration of ferritin in the sample is measured by, the degree of this coloring. (M. C. Revanet; Clin. Chem. vol.29, p.681 (1983)) Instead of chromogen, using a phenolic derivative of general formula (1), 2,3-dihydro-1,4-phthalazinedione or its derivative (b), and an oxidant (d), there is provided an enhanced luminescent reaction with more a greater amount of luminescence. The concentration of ferritin in the sample may be measured by quantifying the light emitted with accuracy and stability.

In competitive heterogeneous immunoassay antibody is immobilized on solid phase carrier such a test tube, glass beads, plastic beads, micro-particles, and the like, then the substance to be assayed in a sample and enzyme labelled antigen of the substance to be assayed are allowed to carry out a competitive reaction therein. As the amount of the enzyme being bound to antibody being immobilized on the solid phase carrier is inversely proportional to the amount of the substance in the sample to be assayed, the amount of the substance to be assayed in the sample may be determined from a calibration curve which is prepared by a standard substance, in advance. In competitive heterogeneous immunoassay whose detail is shown by T. Arakawa et al (*Anal. Biochem.* vol.97p.248(1974)), employing solid phase antigen wherein anticortisol antigen immobilized on Sepharose 4B and cortisol which are labelled by a peroxidase (c), the amount of the peroxidase being bound to the solid phase is assayed by a luminescent reaction maintaining a luminol and hydrogen peroxide, and thus cortisol in the sample is quantified. According to the present invention, a phenolic derivative (a) of general formula (1) is added to this luminescent reaction in order to enhance the luminescent reaction, and thereby maximizing the sensitivity of the measurement by maximized light emission in order to quantify the cortisol in the sample with increased sensitivity.

Accordingly, the present invention provides an assay kit for use in the enhanced luminescent or luminometric assay of the present invention. This assay kit comprises;

(1) a phenolic derivative (a) of general formula (1)
(2) a 2,3-dihydro-1,4-phthalazinedione or its derivative (b)
(3) a peroxidase enzyme(c)
(4) an oxidant (d).

The assay kit may contain other additives as long as they do not inhibit the objects of this invention.

Preferred combination of the assay kit will be each one of those substances mentioned above as preferred for use in the assay. Most preferred embodiment of the assay kit comprises at least one of the peroxidase enzyme (c) and 2,3-dihydro-1,4-phthalazinedione or its derivative (b) coupled to an antibody to the substance to be assayed. The assay kit of this invention may comprise of the above-mentioned (1) to (4) independently, or (1) is previously mixed with either one of (2), (3) and (4). Optionally the assay kit may also contain one or more standard solutions, each containing a known amount of the substance to be assayed, and/or one or more of the preferred buffer solutions. Conveniently the assay kit may include a reaction vessel suitable for use in conjunction with the apparatus used for the determination of the light emission in the course of carrying out the assay. Also conveniently, a mixing device may be included in the assay kit, for use in mixing reactants.

Hereinafter, the present invention is further illustrated in detail in the following examples, although these examples are not to be considered limiting the present invention.

Example 1

The present example illustrates that the chemiluminescent enhancer of the present invention promotes a chemiluminescent reaction between luminol, a coupled form of horseradish peroxidase, and hydrogen peroxide, and substantially increases the light emission compared with that achieved by the luminescent reaction in the absence of enhancer.

First, 0.02 mol/liter (hereinafter, referred to as M) of horseradish peroxidase (Grade I-C, manufactured by Toyobo Co., Ltd., Japan) was dissolved in phosphate buffer (pH 7.2) concentration of the peroxidase in the solution was measured with an absorbance of 403nm to be 0.12 mg/ml. The thus obtained solution was further diluted to 1/10000 by using tile phosphate buffer.

Then, 0.18 g of luminol (manufactured by Tokyo Kasei Co., Ltd. Japan) and 0.1 g each of 4-(cyanomethylthio)phenol, 4-(cyanoethylthio)phenol, 4-(benzylthio)phenol, 4-(methylthio)phenol, 4-(morpholinomethylthio)phenol, 4-cyanomethylthio-2-fluorophenol, 4-cyanomethylthio-2-chlorophenol, 4-cyanomethylthio-2-bromophenol, 4-cyano-methylthio-2-iodophenol; and paraiodophenol as a control were respectively dissolved in liter of Tris/hydrochloride buffer (0.1 M, pH 8.5) to obtain a stock solution.

As an oxidant, hydrogen peroxide was employed. 200 μl of 35% hydrogen peroxide was dissolved in 1 liter of Tris/hydrochloride buffer (0.1M, pH 8.5) to obtain a stock solution.

A luminescence reader (BLR-201 type, made by Aloca Co., Ltd.) was used for measuring a light intensity. The peroxidase solution (containing 1.2 ng of peroxidase) prepared as mentioned above was poured 100 $\mu l$ at a time into test tubes made of glass having a dimension of $12 \times 75$ mm. The test tubes were set in sample holders of the luminescence reader. Then, 250 $\mu l$ of luminol solution containing each enhancer was poured into the respective test tubes. Finally, the hydrogen peroxide solution were poured 250 $\mu l$ at a time into the test tubes, thereby triggered the reaction (reaction temperature: 30° C.). In the same way, a blank test, a test in the absence of the enhancer, and a comparative test using paraiodophenol as the enhancer were conducted. The results are shown in Table 1.

TABLE 1

|  | (1) POD 1.2 ng | (2) POD 0 ng | (1)/(2) |
| --- | --- | --- | --- |
| non enhancer | 0.04 | 0.02 | 2 |
| 4-(cyanomethylthio)phenol | 768.4 | 0.03 | 25613 |
| 4-(cyanoethylthio)phenol | 7.3 | 0.01 | 730 |
| 4-(benzylthio)phenol | 11.1 | 0.02 | 555 |
| 4-(methylthio)phenol | 5.2 | 0.01 | 520 |
| 4-(morpholinomethylthio)phenol | 18.6 | 0.02 | 930 |
| 4-cyanomethylthio-2-fluorophenol | 31.1 | 0.02 | 1555 |
| 4-cyanomethylthio-2-chlorophenol | 37.5 | 0.02 | 1875 |
| 4-cyanomethylthio-2-bromophenol | 27.3 | 0.02 | 1365 |
| 4-cyanomethylthio-2-iodophenol | 29.9 | 0.02 | 1495 |
| paraiodophenol | 27.9 | 0.02 | 1395 |

Remarks:
POD: horseradish peroxidase
Dimension; kilocount

Figure 1:
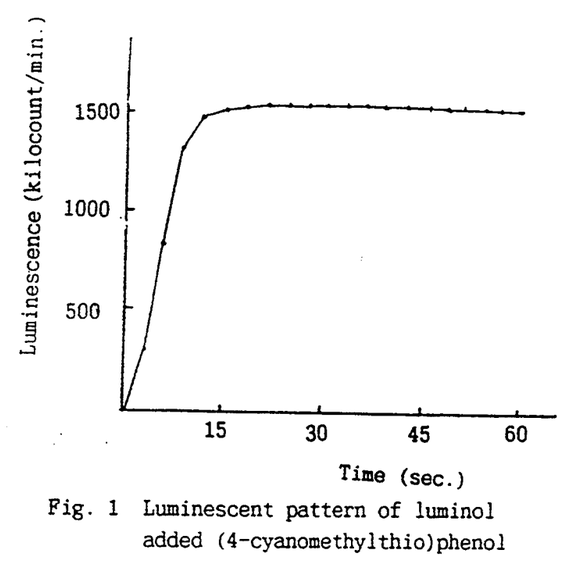
FIG. 1 is a graph showing a luminescent pattern of luminol in the case of adding (4-cyanomethylthio)phenol thereto, an illustration of luminescent reaction of the present invention in Example 1.

The values (kilocount) listed in Table i were obtained by integrating the light emission for one minute from the time when the hydrogen peroxide was poured. A luminescent pattern measured every three seconds in the case that 4-(cyanomethylthio)phenol was added as an enhancer was as shown in FIG. 1. This pattern became constant about 15 seconds after the hydrogen peroxide was poured.

EXAMPLE 2

The comparison of optimum concentrations between the enhancers used in the present invention, such as 4-(cyanomethylthio)phenol, 4-cyanomethylthio-2-fluorophenol, 4-cyanomethylthio-2-chlorophenol, 4-cyanomethylthio-2bromophenol and 4-cyanomethylthio-2-iodophenol, and the conventional enhancer, such as paraiodophenol, was made in the present example.

First, 0.18 g of luminol (Tokyo Kasei Co.) was dissolved in 1 liter of Tris/hydrochloride buffer (0.1M, pH 8.5). Then, 4-(cyanomethylthio)phenol, 4-cyanomethylthio-2-fluorophenol, 4-cyanomethylthio-2-chlorophenol, 4-cyanomethylthio-2-bromophenol, 4-cyanomethylthio-2-iodophenol, and paraiodophenol were respectively dissolved in the thus obtained solution so that each concentration became 0.1 g/dl, 0.05 g/dl, 0.01 g/dl, 0.005 g/dl, and 0.001 g/dl, thereby obtaining stock solutions.

The luminescense reader (Alkca Co.; BLR-201) was used for measuring a light intensity. The peroxidase solution (containing 1.2 ng of peroxidase) prepared as mentioned above was poured 100 $\mu l$ at a time into test tubes made of glass having a dimension of $12 \times 75$ mm. The test tubes were set in sample holders of the luminescense reader. Then, 250 $\mu l$ of luminol solution containing the enhancer of each concentration was poured into the respective test tubes. Finally, the hydrogen peroxide solution was poured 250 $\mu l$ at a time into the test tubes, thereby triggering the reaction (reaction temperature: 30° C.).

The results are shown in Table 2.

Figure 2:
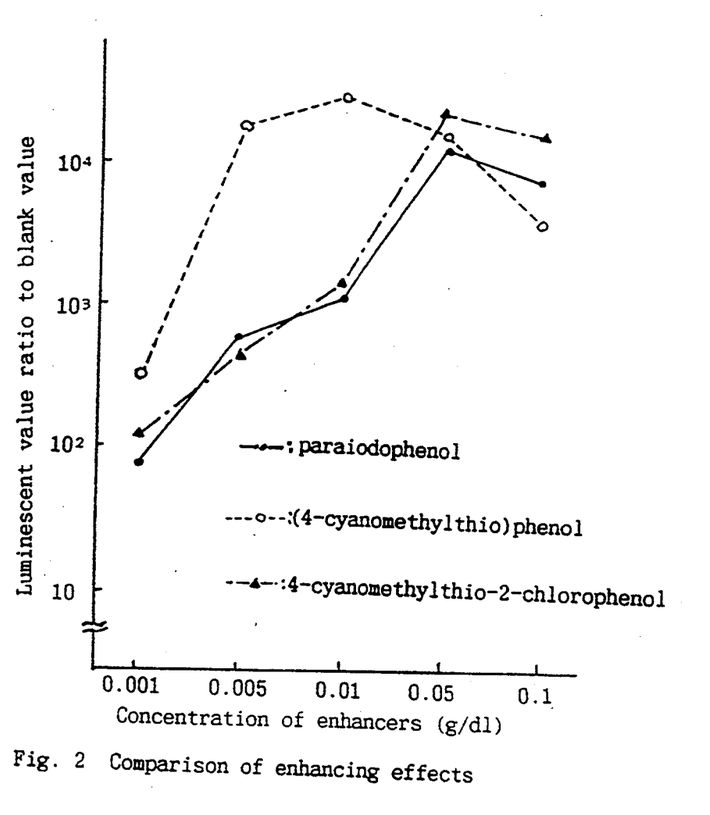
FIG. 2 is a graph showing the comparison of the enhancing effects to the chemiluminescence by (4-cyanomethylthio)phenol, 4-cyanomethylthio-2-chlorophenol, and paraiodophenol in Example 2.

The values (kilocount) listed in Table 2 were obtained by integrating the light emission for one minute from the time when the hydrogen peroxide was poured. FIG. 2 shows a relationship between the respective concentrations of the enhancers and the blank values of the light intensity. From these results, it was found that the 4-(cyanomethylthio)phenol used in the present invention exhibited more excellent performance (the light emission and the ratio of the light emission to the blank value) than the paraiodophenol of the prior art, even when the concentration of the 4-(cyanomethylthio)phenol was 1/10 of that of the paraiodophenol. Moreover, 4-cyanomethylthio-2-fluorophenol, 4-cyanomethylthio-2-chlorophenol, 4-cyanomethylthio-2-bromophenol, and 4-cyanomethylthio-2-iodophenol exhibited more excellent performance than the paraiodophenol, even when the concentrations of the above phenols used in the present invention were the same as that of the paraiodophenol.

TABLE 2

| Enhancer | Sample | g/dl | | | | |
| --- | --- | --- | --- | --- | --- | --- |
| | | 0.1 | 0.05 | 0.01 | 0.005 | 0.001 |
| 4-(cyanomethyl thio)phenol | ① | 107.5 | 307.3 | 768.4 | 386.2 | 4.2 |
| | ② | 0.02 | 0.02 | 0.03 | 0.02 | 0.01 |
| | ①/② | 5375 | 15365 | 25613 | 19310 | 420 |
| 4-cyanomethyl thio-2-fluorophenol | ① | 297.1 | 429.0 | 31.1 | 4.5 | 0.8 |
| | ② | 0.02 | 0.02 | 0.02 | 0.01 | 0.01 |
| | ①/② | 14855 | 21450 | 1555 | 450 | 80 |
| 4-cyanomethyl thio-2-chlorophenol | ① | 338.4 | 455.3 | 37.5 | 6.3 | 1.3 |
| | ② | 0.02 | 0.02 | 0.02 | 0.01 | 0.01 |
| | ①/② | 16920 | 22765 | 1875 | 630 | 130 |
| 4-cyanomethyl thio-2-bromophenol | ① | 316.2 | 396.1 | 27.3 | 5.1 | 0.9 |
| | ② | 0.02 | 0.02 | 0.02 | 0.01 | 0.01 |
| | ①/② | 15810 | 19805 | 1365 | 510 | 90 |
| 4-cyanomethyl thio-2-iodophenol | ① | 351.2 | 439.6 | 29.9 | 6.9 | 1.5 |
| | ② | 0.02 | 0.02 | 0.02 | 0.01 | 0.01 |
| | ①/② | 17560 | 21980 | 1495 | 690 | 150 |
| paraiodophenol | ① | 85.6 | 278.1 | 27.9 | 7.2 | 0.9 |
| | ② | 0.01 | 0.02 | 0.02 | 0.01 | 0.01 |

TABLE 2-continued

| Enhancer | Sample | g/dl | | | | |
|---|---|---|---|---|---|---|
| | | 0.1 | 0.05 | 0.01 | 0.005 | 0.001 |
| | ①/② | 8560 | 13905 | 1395 | 720 | 90 |

Remarks: Dimension; kilocount
① ; light emission POD 1.2 ng
② ; light emission POD 0 ng (blank)
①/② ; the ratio of the light emission to the blank value

EXAMPLE 3

The present example relates to a measurement of α-phetoprotein (hereinafter, referred to as AFP) by two-site chemiluminescent immunoassay in which 4-(cyanomethylthio)phenol is used as a luminescent enhancer, and a solid phase antibody, a peroxidase labelled antibody, luminol, and hydrogen peroxide are combined.

(1) Immobilization of Anti-AFP Antibody on Test Tubes

An anti-AFP antibody (derived from a rabbit; manufactured by Dako Co., Ltd.) was dissolved in carbonate buffer (0.02M, pH 9.5) so as to be 100 μg/ml. The carbonate buffer containing the anti-AFP antibody was poured 500 μl at a time into test tubes made of polystyrene having a dimension of 12×75 mm (manufactured by Nunk Co., Ltd.) and allowed to react for 48 hours at 4° C., thereby immobilizing the antibodies on inner walls of the test tubes. After the reaction was completed, liquid in the test tubes was removed by using an aspirator. The test tubes were washed with 1 ml of a physiological saline three times. Then, 1 ml of phosphate buffer (0.02M, pH 7.2) containing 1% bovine serum albumin (hereinafter, referred to as BSA) was added to each test tube, and kept at 4° C. until they were used.

(2) Preparation of Enzyme Labelled Anti-AFP Antibody

Peroxidase labelled anti-AFP antibody was prepared from horseradish peroxidase (Toyobo Co.; I-C,) and anti-AFP antibody (derived from rabbit, manufactured by Dako Co., Ltd.) by the periodate oxidation method (Nakane et al; *J. Histochem. Cytochem.*, vol.22, p.1,084 (1974)).

(3) Measurement of AFP in the Blood

(i) Enzyme labelled antibody solution

The peroxidase labelled anti-AFP antibody obtained in (2) was diluted with phosphate buffer (0.02M, pH 7.2) containing 1% BSA so as to be a concentration required for the measurement.

(ii) Standard solution

Purified human AFP was diluted with phosphate buffer (0.02M, pH 7.2) containing 1% BSA so that each concentration became 20 ng/ml, 80 ng/ml, 320 ng/ml, and 640 ng/ml.

(iii) Measurement method

An immersed solution in the test tubes in which antibodies were immobilized on the inside walls thereof prepared in (1) was removed by using an aspirator. The test tubes were washed with 1 ml of physiological saline once. Then, 30 μl of standard solution or specimen (serum or plasma) was sampled in the washed test tubes. 500 μl of phosphate buffer (0.02M, pH 7.2) containing 1% BSA was added to the standard solution or specimen in the test tubes and thoroughly stirred, followed by incubation for 30 minutes at 37° C.

After the reaction was completed, the reaction solution was removed by using an aspirator. Then, the test tubes were washed with 1 ml of physiological saline again. The same procedure was repeated three times to remove various serum components in the specimen.

Next, 500 μl of enzyme labelled anti-AFP antibody solution prepared in (i) was poured into the test tubes and thoroughly stirred, followed by the incubation for 30 minutes at 37° C. After the reaction was completed, the reaction solution was removed by using an aspirator. The test tubes were washed with 1 ml of physiological saline again. This procedure was repeated three times to remove unreacted enzyme labelled anti-AFP antibody.

The test tubes washed in the above were set in the sample holders of the luminescense reader. Then, 250 μl of luminol solution containing 4-(cyanomethylthio)-phenol and 250 μl of hydrogen peroxide prepared in Example 1 were poured into the respective test tubes, whereby the chemiluminescent reaction was conducted. The measurement values were obtained by integrating the light emission for one minute.

The light emission at each concentration of the standard solution in the case that the standard solution was used as a specimen is shown in Table 3.

TABLE 3

| Standard AFP (ng/ml) | 0 | 20 | 80 | 320 | 640 |
|---|---|---|---|---|---|
| Light emission (kilocount) | 0.11 | 31.9 | 124.7 | 463.2 | 821.2 |

Figure 3:
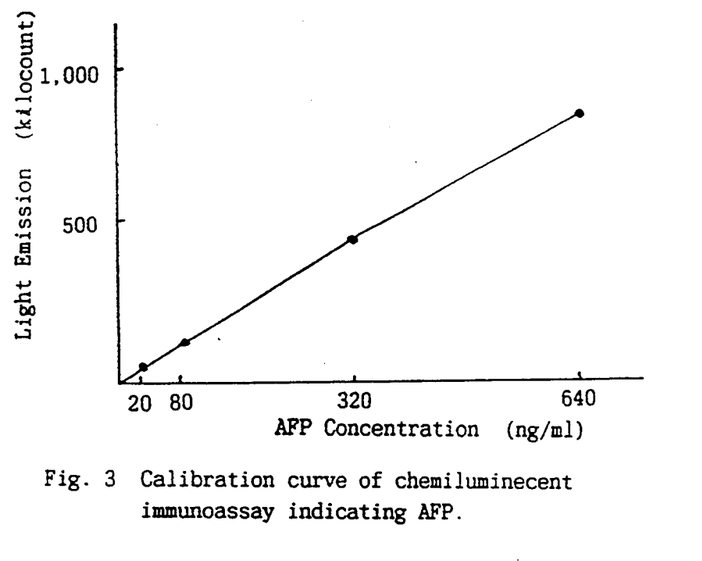
FIG. 3 is a graph showing a calibration curve of chemiluminescent immunoassay indicating AFP.

The AFP concentration was read from a calibration curve (FIG. 3) obtained by plotting a light emission at each concentration of the standard solution.

Figure 4:
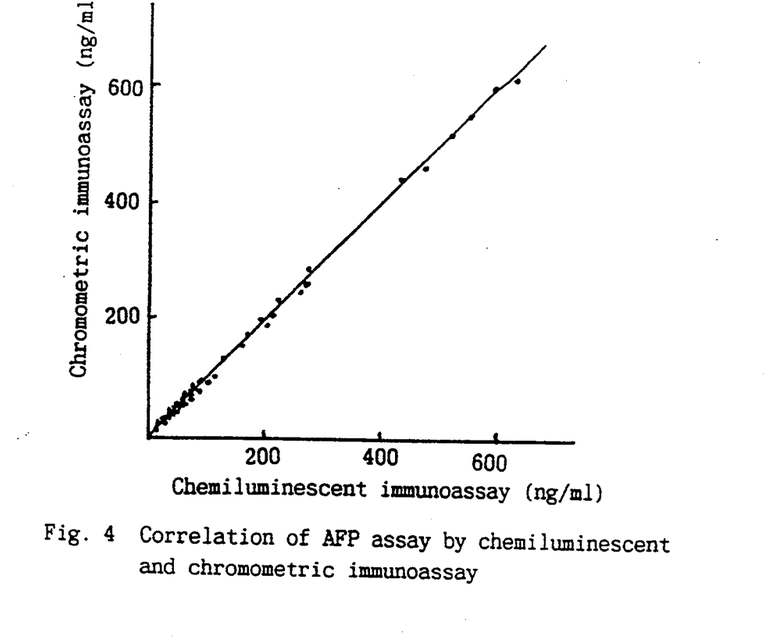
FIG. 4 is a graph showing correlation of the result of AFP assay by chemiluminescent immunoassay and chromometric immunoassay in Example 3.

FIG. 4 shows a relationship between the AFP concentration obtained by measuring the specimen according to the method of the present example and the AFP concentration obtained by measuring the specimen in accordance with chromometric EIA (Enzyme Immunoassay) using the peroxidase labelled anti-AFP antibody.

Example 4

The present example relates to a quantification of thyroxine (T4) by the chemiluminescent immunoassay in which 4-(cyanomethylthio)phenol is used as a luminescent enhancer, and a solid phase antibody, a peroxidase labelled antigen, luminol, and hydrogen peroxide are combined.

(1) Immobilization of anti-T4 Antibody on the Test Tubes

Anti-T4 antibody (derived from rabbit, manufactured by Kallestad Co., Ltd.) was immobilized on the inner walls of the test tubes in the same way as in Example 3.

(2) Preparation of Enzyme Labelled Antigen (T4)

Peroxidase labelled T4 was prepared from horseradish peroxidase (Toyobo Co.; I-C) and T4 (manufactured by Calbiochemistry Co., Ltd.) by the glutaraldehyde method (Abrameas; *Immunochemistry*, vol.6, p.43 (1969)).

(i) Enzyme labelled antigen solution

The peroxidase labelled antigen (T4) obtained in (2) was diluted with barbital buffer (0.1M, pH 8.6) containing 1% BSA and 0.04% 8-anilino-1-naphthalenesulfonic acid ammonium so as to be a concentration required for the measurement.

(ii) Standard solution

T4 (Calbiochemistry Co.) was added to T3 and T4-free serum obtained by treating human serum with activated carbon so that the concentration became 2.0 $\mu g/dl$, 6.0 $\mu g/dl$, 12.0 $\mu g/dl$, and 24.0 $\mu g/dl$ in accordance with the method of Miyai et al., (Miyai et al; *Endocrinol Japan*, vol.27, p.375 (1980)).

(iii) Measurement method

The test tubes were washed in the same way as in Example 3. Then, 20 $\mu l$ of standard solution or specimen (serum or plasma) was sampled in the washed test tubes. 500 $\mu l$ of enzyme labelled antigen solution was added to the standard solution or specimen in the test tubes and thoroughly stirred, followed by incubation for 30 minutes at 37° C.

After the reaction was completed, the reaction solution was removed by using an aspirator. Then, the test tubes were washed with 1 ml of physiological saline again. The same procedure was repeated three times to remove various serum components in the specimen and unreacted enzyme labelled antigen (T4).

The test tubes washed in the above were set in the sample holders of the luminescense reader. The chemiluminescent reaction was conducted in the same way as in Example 3. The measurement values were obtained by integrating light emission for one minute.

The light emission at each concentration of the standard solution in the case that the standard solution was used as a specimen is shown in Table 4.

TABLE 4

| Standard T4 ($\mu g/dl$) | 0 | 20 | 80 | 320 | 640 |
|---|---|---|---|---|---|
| Light emission (kilocount) | 628.4 | 421.2 | 315.3 | 208.4 | 97.3 |

Figure 5:
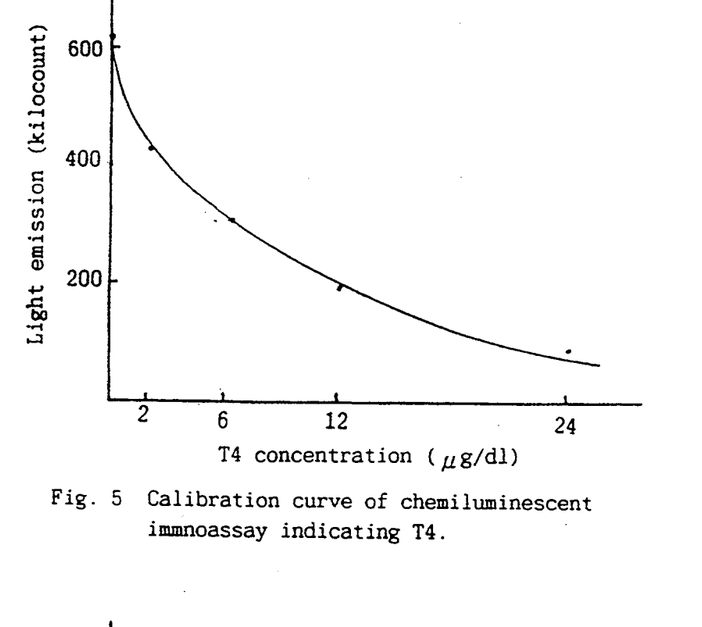
FIG. 5 is a graph showing a calibration curve of chemiluminescent immunoassay indicating T4.

The T4 concentration in the specimen (serum or plasma) was read from a calibration curve (FIG. 5) obtained by plotting a light emission at each concentration of the standard solution.

Figure 6:
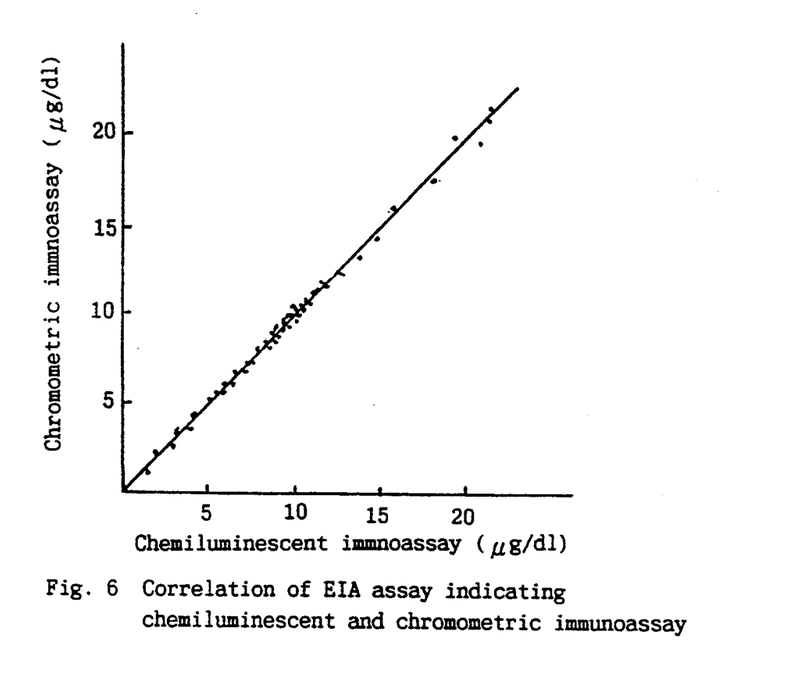
FIG. 6 is a graph showing a correlation of the results of the EIA assay indicating chemiluminescent immunoassay of the present invention and chromometric immunoassay in Example 4.

FIG. 6 shows a relationship between the T4 concentration obtained by measuring the specimen according to the method of the present example and the T4 concentration obtained by measuring the specimen in accordance with chromometric EIA using the peroxidase labelled antigen (T4).

What is claimed is:

1. A luminometric assay involving enhanced luminescent reaction of 2,3-dihydro-1,4-pthalazinedione or a chemiluminescent derivative thereof, a peroxidase enzyme, and an oxidant, comprising:
   (a) mixing a sample containing a substance to be assayed with a ligand-coupled peroxidase enzyme which ligand specifically binds to the substance to be assayed to form a complex;
   (b) separating said complex from unbound ligand-coupled peroxidase enzyme;
   (c) reacting said complex with 2,3-dihydro-1,4-pthalazinedione or a chemiluminescent derivative thereof, an oxidant, and an enhancer selected from the group consisting of 4-(cyanomethylthio)-phenol, its sodium salt, and its potassium salt, thereby causing luminescence; and
   (d) detecting the presence of said luminescence, thereby determining the presence of said substance to be assayed.

2. The luminometric assay according to claim 1, wherein said 2,3-dihydro-1,4-phthalazinedione or a chemiluminescent derivative thereof, is selected from the group consisting of luminol, N-aminohexyl-N-ethylisoluminol, and N-aminobutyl-N-ethylisoluminol.

3. The luminometric assay according to claim 1, wherein the peroxidase enzyme is a horseradish peroxidase.

4. The luminometric assay according to claim 1, wherein the ligand is selected from the group consisting of antigen, antibody, hapten, protein A, avidin, and biotin.

5. The luminometric assay according to claim 1, wherein the oxidant is hydrogen peroxide or perborate.

6. A kit for use in a luminescent or luminometric assay, comprising an enhancer selected from the group consisting of 4-(cyanomethylthio)phenol, its sodium salt, and its potassium salt, 2,3-dihydro-1,4-phthalazinedione or a chemiluminescent derivative thereof, an oxidant, and a peroxidase enzyme.

7. The kit for use in a luminescent or luminometric assay, according to claim 6, wherein the peroxidase enzyme is coupled with a ligand.

8. The kit for use in a luminescent or luminometric assay according to claim 1, wherein said 2,3-dihydro-1,4-phthalazinedione or a chemiluminescent derivative thereof, is selected from the group consisting of luminol, N-aminohexyl-N-ethylisoluminol, and N-aminobutyl-N-ethyl-isoluminol.

9. The kit for use in a luminescent or luminometric assay according to claim 6, wherein the peroxidase enzyme is horseradish peroxidase.

10. The kit for use in a luminescent or luminometric assay according to claim 6, wherein said peroxidase enzyme is coupled to a ligand selected from the group consisting of an antigen, antibody, hapten, protein A, avidin, and biotin.

11. The kit for use in a luminescent or luminometric assay according to claim 6, wherein the oxidant is hydrogen peroxide or perborate.

12. A luminometric assay involving enhanced luminescent reaction of 2,3-dihydro-1,4-pthalazinedione or a chemiluminescent derivative thereof, a peroxidase enzyme, and an oxidant, comprising:
   (a) mixing a sample containing an antigen to be assayed with a solid phase carrier having an antibody which specifically binds to said antigen to be assayed immobilized thereon, and allowing said antigen to be assayed in the sample to specifically bind to said antibody immobilized on said solid carrier to form a complex;
   (b) adding an antibody coupled peroxidase enzyme which antibody specifically binds to said complex;

(c) separating said complex immobilized on the solid phase carrier from unbound antibody coupled peroxidase enzyme;

(d) reacting said complex with an oxidant, 2,3-dihydro-1,4-pthalazinedione or a chemiluminescent derivative thereof, and an enhancer selected from the group consisting of 4-(cyanomethylthio)-phenol, its sodium salt, and its potassium salt, thereby causing luminescence; and (e) measuring the amount of luminescence and determining therefrom the amount of said antigen to be assayed.

13. A luminometric assay involving enhanced luminescent reaction of 2,3-dihydro-1,4-pthalazinedione or a chemiluminescent derivative thereof, a peroxidase enzyme, and an oxidant, comprising:

(a) mixing a sample containing an antigen to be assayed with the antigen coupled peroxidase enzyme;

(b) reacting said antigen to be assayed in the sample and said antigen-coupled peroxidase enzyme competitively with an antibody which specifically binds to the antigen immobilized on a solid phase carrier to form a complex;

(c) separating said complex immobilized on the solid phase carrier from unbound antigen-coupled peroxidase enzyme;

(d) reacting said complex with an oxidant, 2,3-dihydro-1,4-pthalazinedione or a chemiluminescent derivative thereof, and an enhancer selected from the group consisting of 4-(cyanomethylthio)-phenol, its sodium salt, and its potassium salt, thereby causing luminescence; and (e) measuring the amount of luminescence and determining therefrom the amount of the antigen to be assayed.

14. A luminometric assay involving enhanced luminescent reaction of 2,3-dihydro-1,4-pthalazinedione or a chemiluminescent derivative thereof, a peroxidase enzyme, and an oxidant, comprising:

(a) mixing a sample containing an antigen to be assayed with a solid phase carrier having said antigen to form a mixture;

(b) reacting said antigen to be assayed in the sample and the antigen immobilized on said solid-phase carrier competitively with an antibody-coupled peroxidase enzyme which antibody competes for specific binding to the antigen to be assayed and the antigen on the solid-phase carrier to form a complex on said solid phase carrier;

(c) Separating said complex immobilized on the solid phase carrier from the mixture;

(d) reacting said complex with an oxidant, 2,3-dihydro-1,4-pthalazinedione or a chemiluminescent derivative thereof, and an enhancer selected from the group consisting of 4-(cyanomethylthio)-phenol, its sodium salt, and its potassium salt, thereby causing luminescence; and (e) measuring the amount of luminescence and determining therefrom the amount of the antigen to be assayed.

* * * * *